(12) United States Patent
Nagashima et al.

(10) Patent No.: US 6,261,592 B1
(45) Date of Patent: Jul. 17, 2001

(54) PHYTASE HAVING A LOW MICHAELIS CONSTANT FOR PHYTIC ACID FROM MONASCUS

(75) Inventors: Tadashi Nagashima; Satoshi Kuroyanagi; Tadanori Yamamura, all of Aichi; Hideharu Anazawa, Tokyo; Yoko Kato, Tokyo; Seiji Sugimoto, Tokyo; Keiichi Yano, Tokyo, all of (JP)

(73) Assignees: Kyowa Hakko Kogyo Co., LTD, Tokyo; Shin Nihon Chemical Co., LTD, Anjo, both of (JP)

( * ) Notice: Subject to any disclaimer, the term of this patent is extended or adjusted under 35 U.S.C. 154(b) by 0 days.

(21) Appl. No.: 09/269,062

(22) PCT Filed: Sep. 25, 1997

(86) PCT No.: PCT/JP97/03414

§ 371 Date: Mar. 18, 1999

§ 102(e) Date: Mar. 18, 1999

(87) PCT Pub. No.: WO98/13480

PCT Pub. Date: Apr. 2, 1998

(30) Foreign Application Priority Data

Sep. 25, 1996 (JP) .................................................. 8-253564

(51) Int. Cl.[7] ............................ A23K 1/165; A23K 1/18; A61K 38/46; C12N 9/14
(52) U.S. Cl. ......................... 424/442; 424/94.6; 426/807; 435/195
(58) Field of Search .................................... 435/196, 195; 424/445, 94.6; 426/807

(56) References Cited

U.S. PATENT DOCUMENTS 3,297,548  1/1967  Ware et al. ............................ 435/196

FOREIGN PATENT DOCUMENTS

91/05053    4/1991  (WO) .
WO 94/03072  2/1994  (WO) .
WO 94/03612  2/1994  (WO) .

OTHER PUBLICATIONS

Hara, et al. A New Type of Phytase from Pollen of *Typha latifolia*L., Agric, Biol. Chem, 49 (12), 3539–3544, Jun. 5, 1985.
Ullah, A.H., et al., "Extracellular Phytase (E.C. 3.1.3.8) from *Aspergillus ficuum* NRRL 3135: Purification and Characterization," Preparative Biochemistry, vol. 17, No. 1, pp. 63–91 (1987).

Gibson, D.M., et al., "Purification and Characterization of Phytase from Cotyledons of Germinating Soybean Seeds," Archives of Biochemistry & Biophysics, vol. 260, No. 2, pp. 503–513 (1988).
Martin, C.J., et al., "Inositol Hexaphosphate and its Cu(II) Coordinate Complex as Inhibitors of Intestinal Alkaline Phosphatase," Research of Communications in Chemical Pathology & Pharmacology, vol. 65, No. 3, pp. 289–296 (1989).
Martin, C.J., et al., "Reversible Inhibition of Intestinal Alkaline Phosphatase by Inositol Hexaphosphate and Its Cu(II) Coordinate Complexes," Journal of Inorganic Biochemistry, vol. 42, No. 3, pp. 177–184 (1991).
Guillemette, G., et al., "Intracelluar Receptolrs for Inositol 1,4,5–Trisphoshate in Angiotensin II Target Tissues," Journal of Biological Chemistry, vol. 262, No. 3, pp. 1010–1015 (1987).
Segueilha, L., et al., "Purification and Properties of the Phytase from *Schwanniomyces castellii*, " Journal of Fermentation and Bioengineering, vol. 74, No. 1, pp. 7–11 (1992).
Ehrlich, K.C., et al., "Identification and Cloning of a Second Phytase Gene (phyB) from *Aspergillus niger* (*ficuum*)," Biochemical and Biophysical Research Communications, vol. 195, No. 1, pp. 53–57 (1993).
Ullah, A.H., "Production, Rapid Purification and Catalytic Characterization of Extracellular Phytase from *Aspergillus ficuum*," Preparative Biochemistry, vol. 18, No. 4, pp. 443–458 (1988).
Shimizu, M., "Purification and Characterization of Phytase and Acid Phosphatase Produced by *Aspergillus oryzae* K1," Biosci. Biotech. Biochem., vol. 57, No. 8, pp. 1364–1365 (1993).
T.S. Nelson et al., "Effect of Supplemental Phytase on the Utilization of Phytase Phosphorus by Chicks", J. Nutrition 101, pp. 1289–1293, 1971.
C.S. Piddington et al., "The cloning and sequencing of the genes encoding phytase (phy) and pH . . . var. awamori", Gene. 133, 1993, pp. 55–62.
W. van Hartingsveldt et al., "Cloning, characterization and overexpression of the phytase–encoding gene (phyA) of *Aspergillus niger*", Gene. 127, 1993, pp. 87–94.

*Primary Examiner*—David M. Naff
*Assistant Examiner*—Mike Meller
(74) *Attorney, Agent, or Firm*—Foley & Lardner (57) ABSTRACT

Provided is an isolated phytase derived from a microorganism. The microorganism is preferably from the genus Monascus. The phytase has a Michaelis constant of 10 to 110 $\mu$M when phytic acid is used as a substrate. A process for producing the phytase also is provided, as is an animal feed comprising the phytase.

7 Claims, 12 Drawing Sheets

SEQUENCE LISTING

<160> NUMBER OF SEQ ID NOS: 1

<210> SEQ ID NO 1
<211> LENGTH: 17
<212> TYPE: PRT
<213> ORGANISM: Monascus anka -continued

```
<400> SEQUENCE: 1

Phe Gln Ser Val Ile Ser Glu Lys Gln Phe Ser Gln Glu Phe Leu Asp
 1               5                  10                  15
Asn
```

PHYTASE HAVING A LOW MICHAELIS CONSTANT FOR PHYTIC ACID FROM MONASCUS

TECHNICAL FIELD

The present invention relates to inexpensive phytases with low Michaelis constants (abbreviated hereinafter to Km) for phytic acid, which decompose phytic acid as anti-trophic factor contained in feed thereby improving the nutritive values of feed and simultaneously enabling efficient utilization of phosphate released by said decomposition.

BACKGROUND ART

Phosphorus is an element essential for every organism. Phosphorus is included in plant-derived feed used in breeding of domestic animals, and 50 to 70% of the phosphorus is present as phytic acid. Phytic acid occurring in a large amount in plant seeds is a major storage substance of phosphate. However, phytic acid is excreted without digestion and absorption in digestive organs in single-stomach animals such as pigs, chickens etc., so its phosphorus is not utilized at all although it is a major storage substance of phosphate. Accordingly, inorganic phosphate is added to feed for single-stomach animals for the purpose of growth promotion. However, addition of phosphate to feed results in an increase in the amount of phosphorus in feces. In recent years, as production of domestic animals is increased, feces from domestic animals are increased to cause an environmental problem in all over the world. In particular, phosphorus contained in feces is mentioned as a cause for the phenomenon of eutrophication in lakes and marshes, and the amount of excreted phosphorus comes to be regulated and there arises the necessity for dealing with it.

Further phytic acid chelates with divalent metals important as nutritious sources, such as magnesium, calcium, zinc, iron etc. to make them hardly adsorbed into animals, resulting in reduction of the nutritive values of feed. Accordingly, phytic acid is considered as an anti-trophic factor.

From the foregoing, improvements in the nutritive values of feed are attempted by treating feed with an enzyme for hydrolyzing phytic acid into inositol and inorganic phosphate thereby permitting the phytic acid to release the phosphate to substitute it for conventionally added phosphate whereby the amount of phosphorus in feces is decreased, and phytic acid as an anti-trophic factor is decomposed [U.S. Pat. No. 3,297,548 (1967), J. Nutrition 101, 1289–1294 (1971)]. Microorganisms known to produce phytase (enzyme decomposing phytic acid) include bacteria such as *Bacillus subtilis* and Pseudomonas, yeasts such as *Saccharomyces cerevisiae*, and filamentous fungi such as *Aspergillus terreus*, *Aspergillus ficuum* and *Aspergillus awamori*. With respect to the phytase derived from *Aspergillus ficuum*, its purification and biochemical properties are described in Preparative Biochem., 18, 443–458 (1988) and its gene and amino acid sequence are described in Gene, 127, 87–94 (1993). With respect to the phytase derived from *Aspergillus awamori*, its nucleotide sequence and amino acid sequence are described in Gene, 133, 55–62 (1993).

In order to demonstrate the ability possessed by an enzyme, it is necessary for the concentration of its substrate to be higher than the Michaelis constant (Km), and in the case of enzymes having the same maximum reaction rate (Vmax), an enzyme having a lower Km value does not reduce the reaction rate even at lower substrate concentration as compared with an enzyme having a higher Km value. That is, an enzyme having a lower Km value can maintain the sufficient decomposition rate even at lower substrate concentration, and the amount of the substrate not decomposed can be minimized as compared with an enzyme having a higher Km value.

The Michaelis constants (Km) of known phytases derived from filamentous fungi are 250 $\mu$M for *Aspergillus ficuum* (WO 91/05053) and 330 $\mu$M *Aspergillus oryzae* (Biosci. Biotech. Biochem., 57, 1364–1365 (1993)).

On one hand, acidic phosphatases are purified from various microorganisms and their properties are reported, and for example, 2 acidic phosphatases derived from *Aspergillus ficuum* are purified and their properties are examined [Prep. Biochem., 18, 37–65 (1988)]. However, said acidic phosphatases cannot use phytic acid as a substrate, so their utilization for the purpose of improving the nutritive values of feed as described above is not feasible.

Under the circumstances described above, there is a need for phytase which decomposes phytic acid as an anti-trophic factor contained in feed thereby improving the nutritive values of feed and simultaneously enabling efficient utilization of phosphate released by said decomposition.

DISCLOSURE OF THE INVENTION

Accordingly, the object of the present invention is to provide phytases having low Km values for phytic acid and a process for producing said phytases.

As a result of their extensive study for solving the problems described above, from microorganisms belonging to the genus Monascus, the present inventors found novel phytases having Km values of 10 to 110 $\mu$M when phytic acid was used as a substrate, and they revealed the properties thereof and established a process for producing said phytases to complete the present invention.

That is, the present invention relates to novel phytases having Km values of 10 to 110 $\mu$M and a process for producing said phytases.

Specific examples of the novel phytases of the invention include 3 phytases having the following physicochemical properties:

1. Phytase I:
1) Km: 27 $\mu$M when phytic acid is used as a substrate;
2) optimum pH: pH 5.5;
3) pH stability: stable in the range of pH 5.5 to 6.5;
4) optimum temperature: 50° C.;
5) temperature stability: stable up to 35° C.;
6) substrate specificity: acting on phytic acid, p-nitrophenylphosphate, D-glucose-6-phosphate, fructose-6-phosphate, D-myo-inositol-2-phosphate, D-myo-inositol-1-phosphate, D-myo-inositol-1,4-diphosphate, and adenosine triphosphate as the substrate;
7) molecular weight: about 80 to 100 kDa (gel filtration method); and
8) isoelectric point: pI 5.7 (chromatofocusing method).

2. Phytase II:
1) Km: 20 $\mu$M when phytic acid is used as a substrate;
2) optimum pH: pH 6.0;
3) pH stability: stable in the range of pH 6.0 to 7.0;
4) optimum temperature: 50° C.;
5) temperature stability: stable up to 50° C.;
6) substrate specificity: acting on phytic acid, p-nitrophenylphosphate, D-glucose-6-phosphate, fructose-6-phosphate, D-myo-inositol-2-phosphate, D-myo-inositol-1-phosphate, D-myo-inositol-1,4-diphosphate, and adenosine triphosphate as the substrate;
7) molecular weight: about 120 kDa (gel filtration method); and 8) isoelectric point: pI 4.8 (chromatofocusing method).
3. Phytase III:
1) Km: 107 $\mu$M when phytic acid is used as a substrate;
2) optimum pH: pH 2.5;
3) pH stability: stable in the range of pH 2.0 to 8.0;
4) optimum temperature: 45° C.;
5) temperature stability: stable up to 60° C.;
6) substrate specificity: acting on p-nitrophenylphosphate, phytic acid, D-glucose-6-phosphate, fructose-6-phosphate, D-myo-inositol-2-phosphate, D-myo-inositol-1-phosphate, D-myo-inositol-1,4-diphosphate, and adenosine triphosphate as the substrate;
7) molecular weight: about 140 kDa (gel filtration method); and
8) isoelectric point: pI 5.2 (chromatofocusing method); and
9) N-terminal amino acid sequence: shown in SEQ ID NO:1.

The microorganisms used in the present invention may be any microorganisms producing the novel phytases having Km values of 10 to 110 $\mu$M when phytic acid is used as a substrate, and examples are microorganisms belonging to the genus Monascus. Specifically, *Monascus anka* IFO 30873 can be mentioned. Further, animal cells having the ability to produce the novel phytases, which have Km values of 10 to 110 $\mu$M when phytic acid is used as a substrate, can also be used in the present invention.

The microorganism having the ability to produce the novel phytase is cultured in a conventional culture method until the novel phytase is formed and accumulated, and the novel phytase is recovered from the culture whereby the novel phytase can be produced. Hereinafter, the microorganism or mutant used for producing the novel phytase is called the novel phytase-producing organism.

If the novel phytase-producing organism is a prokaryote such as *Escherichia coli* or an eukaryote such as filamentous fungus, yeast etc., the medium for culturing said microorganism may be a natural or synthetic medium insofar as the medium contains a carbon source, a nitrogen source, and inorganic salts etc. which can be assimilated by the microorganism and in which the microorganism can be efficiently cultured.

The carbon source may be any one which can be assimilated by the microorganism and includes glucose, fructose, sucrose, molasses containing such sugar, hydrocarbons such as starch, starch hydrolysates etc., organic acids such as acetic acid, propionic acid etc., and alcohols such as ethanol, propanol etc.

The nitrogen source includes ammonia, ammonium salts of various inorganic and organic acids, such ammonium chloride, ammonium sulfate, ammonium acetate, ammonium phosphate etc. and other nitrogenous compounds, as well as peptone, meat extract, yeast extract, corn steep liquor, casein hydrolysates, soybean cake, soybean cake hydrolysates, and a wide variety of microorganisms obtained by fermentation and digested materials thereof.

Inorganic materials include potassium dihydrogen phosphate, dipotassium hydrogen phosphate, magnesium phosphate, magnesium sulfate, sodium chloride, ferrous sulfate, manganese sulfate, copper sulfate, calcium carbonate etc.

Further, a medium containing wheat bran, rice bran etc. as the carbon, nitrogen and inorganic sources supplemented with suitable salts can be used as a medium in culturing filamentous fungi.

Culture is conducted under aerobic conditions in shaking culture or in submerged spinner culture under aeration. The culture temperature is preferably 15 to 40° C., and the culturing period is usually 16 to 96 hours. The pH during culture is maintained in the range of 3.0 to 9.0. Adjustment of the medium pH is conducted with inorganic or organic acid, alkali solution, urea, calcium carbonate or ammonia.

During culture, antibiotics such as ampicillin, tetracycline etc. may be added to the medium.

If filamentous fungi are to be cultured in a medium containing solid components such as wheat bran etc., the filamentous fungi are inoculated, mixed sufficiently with the solid components, and spread as a thin layer on a large number of aluminum or stainless steel trays in a cellar and cultured under the controlled conditions of temperature, humidity and ventilation. Specifically, the fungi are subjected to stationary culture in a culture chamber under 100% humidity at 25 to 35° C. for 3 to 10 days.

If the novel phytase-producing organism is animal cells, the medium for culturing the animal cells includes generally used RPMI 1640 medium, Eagle's MEM medium, and mediums containing fetal bovine serum in the above mediums, etc.

Culture is conducted under such conditions as in the presence of 5% $CO_2$ etc. The culture temperature is preferably 35 to 37° C., and the culturing period is usually 3 to 7 days.

During culture, antibiotics such as kanamycin, penicillin etc. may be added to the medium.

To isolate and purify the novel phytase from the culture of the novel phytase-producing organism, conventional enzyme isolation and purification methods may be used.

For example, if the novel phytase is accumulated in cells of the novel phytase-producing organism, the cells are collected from the culture by centrifugation, then washed and disrupted by a sonicator, a French press, a Manton-Gaulin homogenizer, a dynomill or the like whereby a cell-free extract is obtained. A supernatant obtained by centrifuging the cell-free extract is subjected to salting-out with e.g. sulfate ammonium, desalting, precipitation with an organic solvent, anion-exchange chromatography on resin such as diethylaminoethyl (DEAE)-Sepharose and DIAION HPA-75 (Mitsubishi Chemical Industries Ltd.), cation-exchange chromatography on resin such as S-Sepharose FF (Pharmacia), hydrophobic chromatography on resin such as butyl Sepharose and phenyl Sepharose, gel filtration on molecular sieves, chromatofocusing and electrophoresis such as isoelectric focusing, whereby a purified enzyme preparation can be obtained.

Analysis of the structure of the purified enzyme preparation can be effected by techniques generally used in protein chemistry, for example techniques described in "Protein Structural Analysis for Gene Cloning" authored by Hisashi Hirano and published by Tokyo Kagaku Dojin (1993).

If the novel phytase is extracellularly secreted, the culture is subjected to e.g. centrifugation to give a soluble fraction. If solid components such as wheat bran etc. are present in the medium ingredients, the novel phytase is extracted with hot water or the like and subjected to techniques such as centrifugation to give a soluble fraction. From this soluble fraction, a purified enzyme preparation of the novel phytase can be obtained by the same techniques as in isolation and purification from the supernatant of the cell-free extract as described above.

In the present invention, the activity of the novel phytase can be determined according to a standard activity measurement method (see the Reference Example below).

Further, the Km value of the novel phytase can be determined by the Lineweaver-Burk plot in which the activity of the novel phytase, as determined by the standard activity measurement method, is plotted at varying concentrations of the substrate.

The novel phytase of the invention can be utilized in various steps required for converting a salt of phytate into inositol and inorganic phosphate, for example in producing animal feed, soybean processing, liquid feed for pigs and poultry, and inositol or inositol monophosphate from salts of phytate.

Animal feed containing the novel phytase of the invention can be produced by mixing said enzyme with carriers such as wheat chaff, drying the mixture in a spraying column or a fluidized bed, and adding osmotic pressure stabilizers such as sorbitol and preservatives such as benzoic acid to the dried material. The amount of the novel phytase in animal feed is 10 to 5000 U, preferably 100 to 1000 U, per kg of the animal feed.

BEST MODE FOR CARRYING OUT THE INVENTION

Hereinafter, the present invention is described in detail by reference to the Examples. However, the present invention is not limited to the Examples.

REFERENCE EXAMPLE
(Method for Measuring Phytase Activity)

In the present invention, the standard activity measurement of the phytase was conducted in the following manner.

0.5 ml of 0.2 M acetate buffer, pH 5.5 (or glycine-HCl buffer, pH 2.5 in the case of examination of the acidic phosphatase activity of decomposing phytic acid) containing 2.5 mM sodium phytate (Sigma) was kept at 37° C. for 5 minutes, and 0.5 ml of an enzyme solution was added to initiate the reaction (finally 1.25 mM sodium phytate-0.1 M acetate buffer, pH 5.5, or 0.1 M glycine-HCl buffer, pH 2.5). After kept at 37° C. for 20 minutes, 2 ml of an enzyme reaction termination solution (i.e. a mixture consisting of 10 mM ammonium molybdate, 5 N sulfuric acid, and acetone at the ratio of 1:1:2) was added to terminate the reaction, and 0.1 ml of 1 M citric acid was added and mixed with the reaction solution. The absorbance of this solution at 380 nm was measured by a spectrophotometer (Hitachi U-2000). 1 unit of the phytase activity is defined as the amount of the enzyme allowing to release of 1 $\mu$mol inorganic phosphorus per minute.

Example 1
(Production of Phytases)

Into a 2000 ml Erlenmeyer flask, 200 ml of a phytase production medium [1% sucrose, 0.2% $NaNO_3$, 0.05% $MgSO_4 \cdot 7H_2O$, 0.05% KCl, 0.001% $FeSO_4 \cdot 7H_2O$, 0.1% corn steep liquor (C. S. L.), pH 5.5] was introduced, capped with a silicone sponge stopper, and sterilized at 120° C. for 20 minutes. Hyphae of *Monascus anka* IFO30873 were inoculated into it and subjected to stationary culture for 10 days to produce phytases. As a crude phytase solution, 980 ml of the resulting culture was used and about 6 units of phytases were thus obtained.

Example 2
(Purification of the Phytases)

The crude phytase solution was desalted by passing it through an Ultrafilter (an exclusion molecular weight of 10,000, Advantec). The resulting enzyme solution was applied to a DEAE-Sepharose F. F. (Pharmacia) column previously equilibrated with 20 mM MES buffer, pH 6.0 (Katayama Kagaku). After washed with 20 mM MES buffer (pH 6.0), phytases I and III were eluted with 20 mM MES buffer (pH 6.0) containing 0.05 M NaCl. Further, phytase II was eluted with 20 mM MES buffer (pH 6.0) containing 0.1 M NaCl. Each enzyme solution thus separated was desalted and concentrated about 20-fold respectively with an Ultrafilter (an exclusion molecular weight of 10,000, Advantec). Further, each enzyme was applied to a DEAE-Sepharose F. F. (Pharmacia) column previously equilibrated with 20 mM MES buffer (pH 6.0). After washed with 20 mM MES buffer (pH 6.0), the protein was eluted with a linear gradient of 0 to 0.3 M NaCl whereby phytase I, II and III fractions were obtained. Each of the enzyme solutions thus obtained was concentrated about 20-fold with an Ultrafilter (an exclusion molecular weight of 10,000, Advantec) and applied to a TOYO-pearl HW-55F (Tosoh Corporation) column previously equilibrated with 20 mM MES buffer, pH 6.0 containing 0.05 M KCl. Phytases I, II and III were eluted respectively with 20 mM MES buffer (pH 6.0) containing 0.05 M KCl.

Phytases I, II and III were purified respectively in the steps described above.

Example 3
(Measurement of Km of Phytases I, II and III)

The purified phytases I, II and III were measured according to the standard activity measurement method where phytic acid was used as a substrate at a varying concentration in the range of 0.00625 to 0.8 mM. The Lineweaver-Burk reciprocal of the result was plotted to determine Km. The Km values of phytases I, II and III for phytic acid were 27, 20 and 107 $\mu$M.

Example 4
(Physicochemical Properties of Phytases I, II and III)

Figure 1:
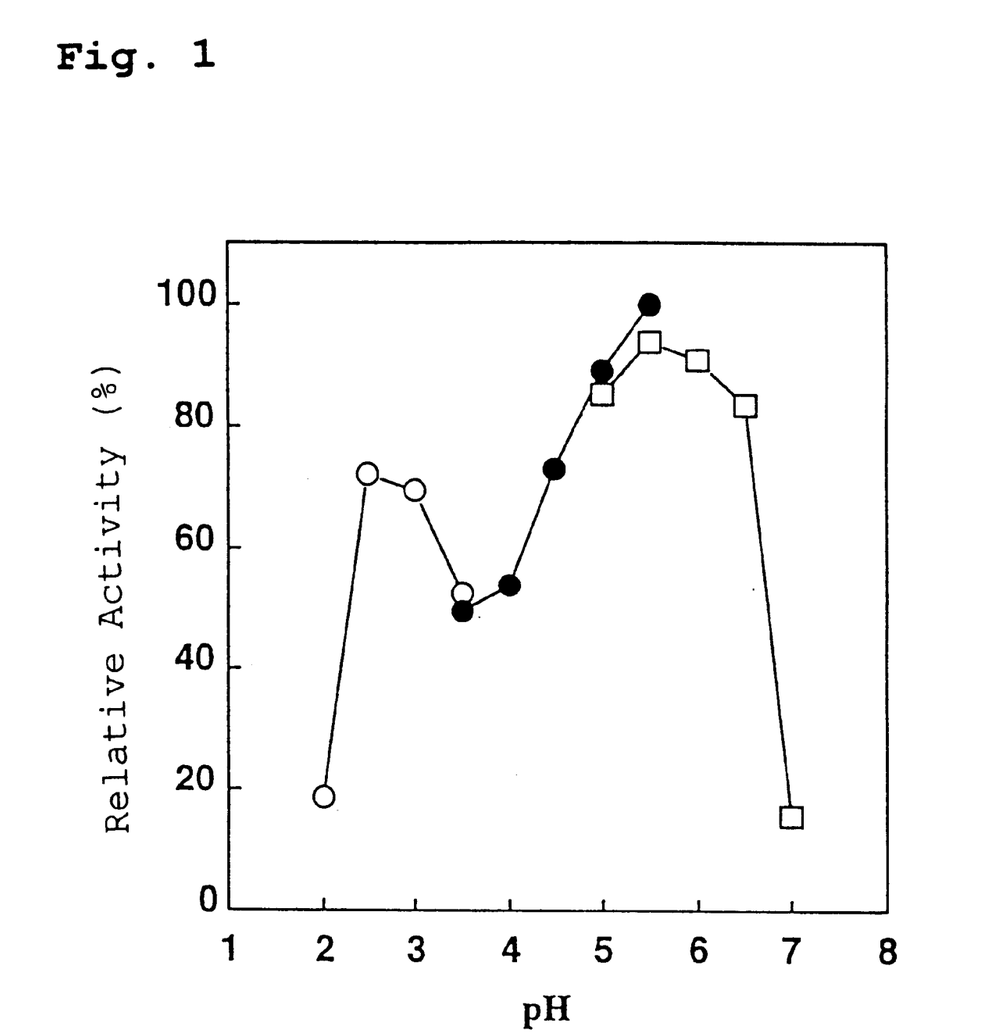
FIG. 1 shows the optimum pH of phytase I.
Figure 2:
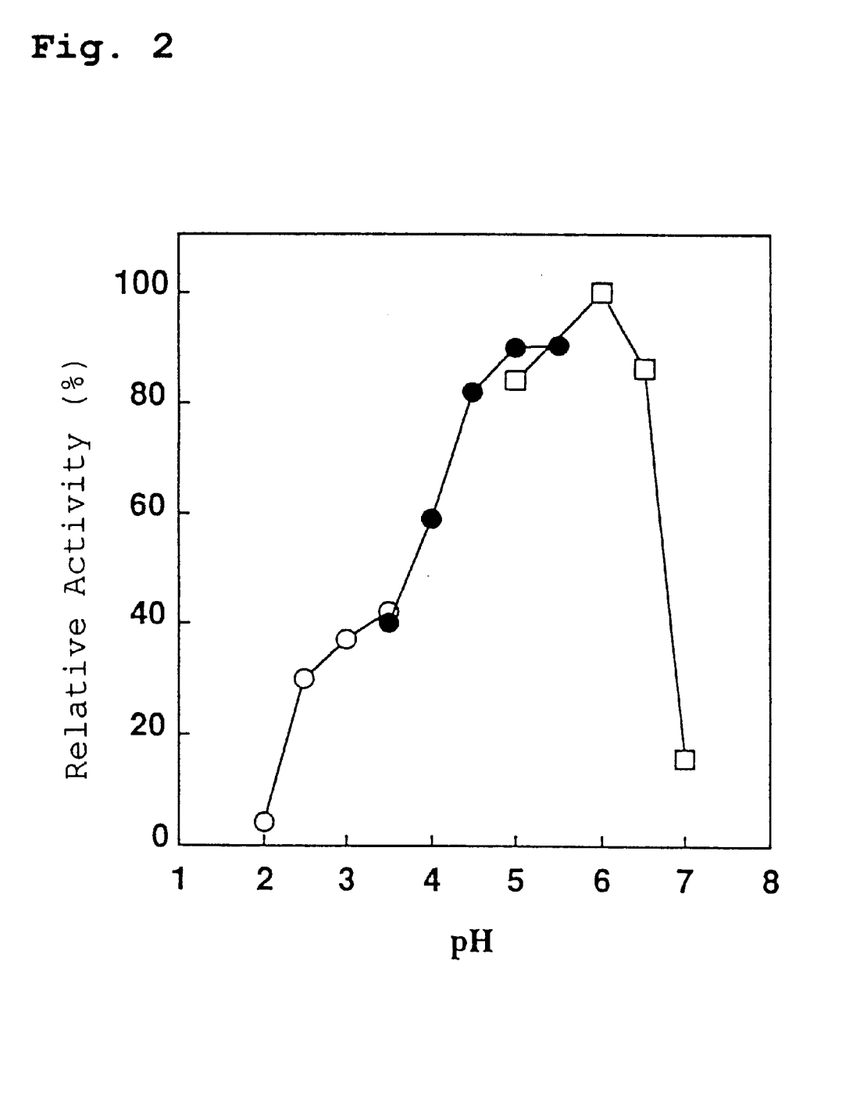
FIG. 2 shows the optimum pH of phytase II.
Figure 3:
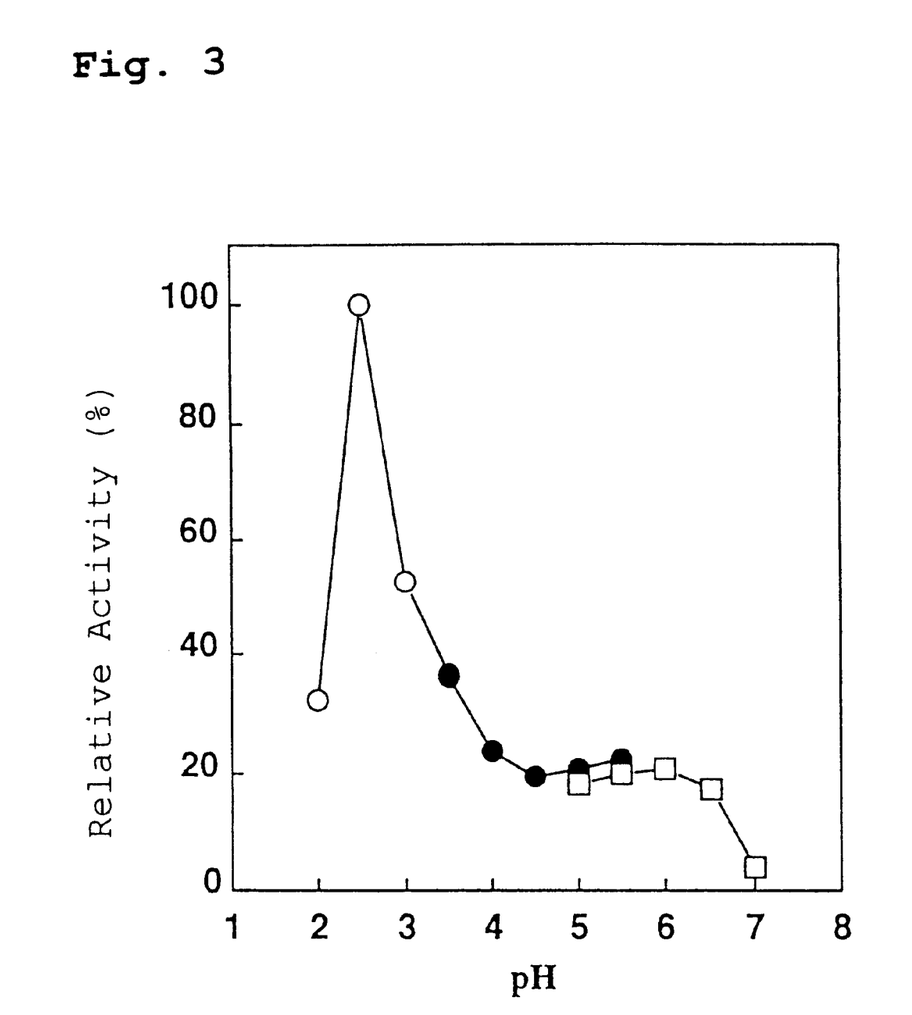
FIG. 3 shows the optimum pH of phytase III.

① Optimum pH: The buffer in the standard activity measurement method was replaced by 0.2 M buffer below, and the activity at each pH was measured according to the standard activity measurement method.

| Glycine-HCl buffer | pH 2.0 to 3.5 |
| Acetic acid-sodium acetate buffer | pH 3.5 to 5.5 |
| MES buffer (Good buffer) | pH 5.0 to 7.0 |
| Tris-HCl buffer | pH 7.0 to 9.0 |

The results are shown in FIGS. 1, 2 and 3.

Phytases I, II and III exhibited the maximum activity at pH 5.5, pH 6.0 and pH 2.5, respectively.

Figure 4:
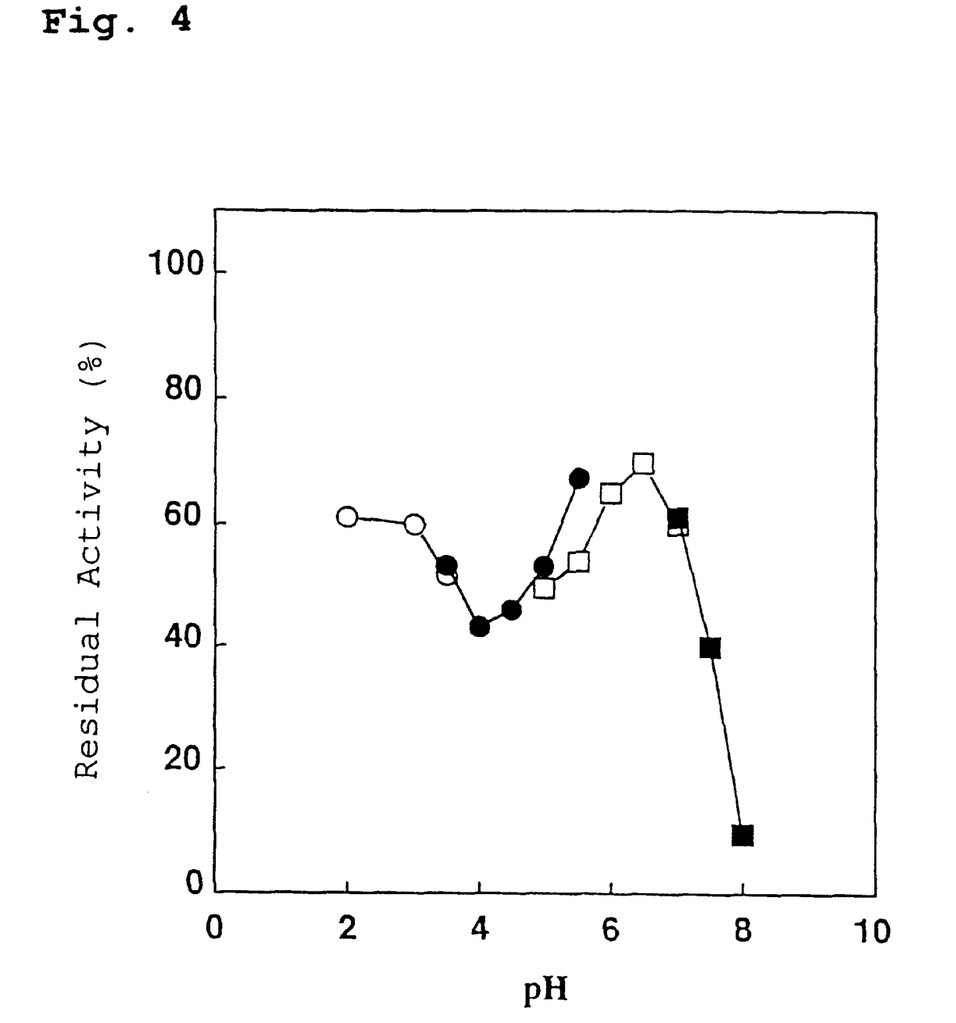
FIG. 4 shows the pH stability of phytase I.
Figure 5:
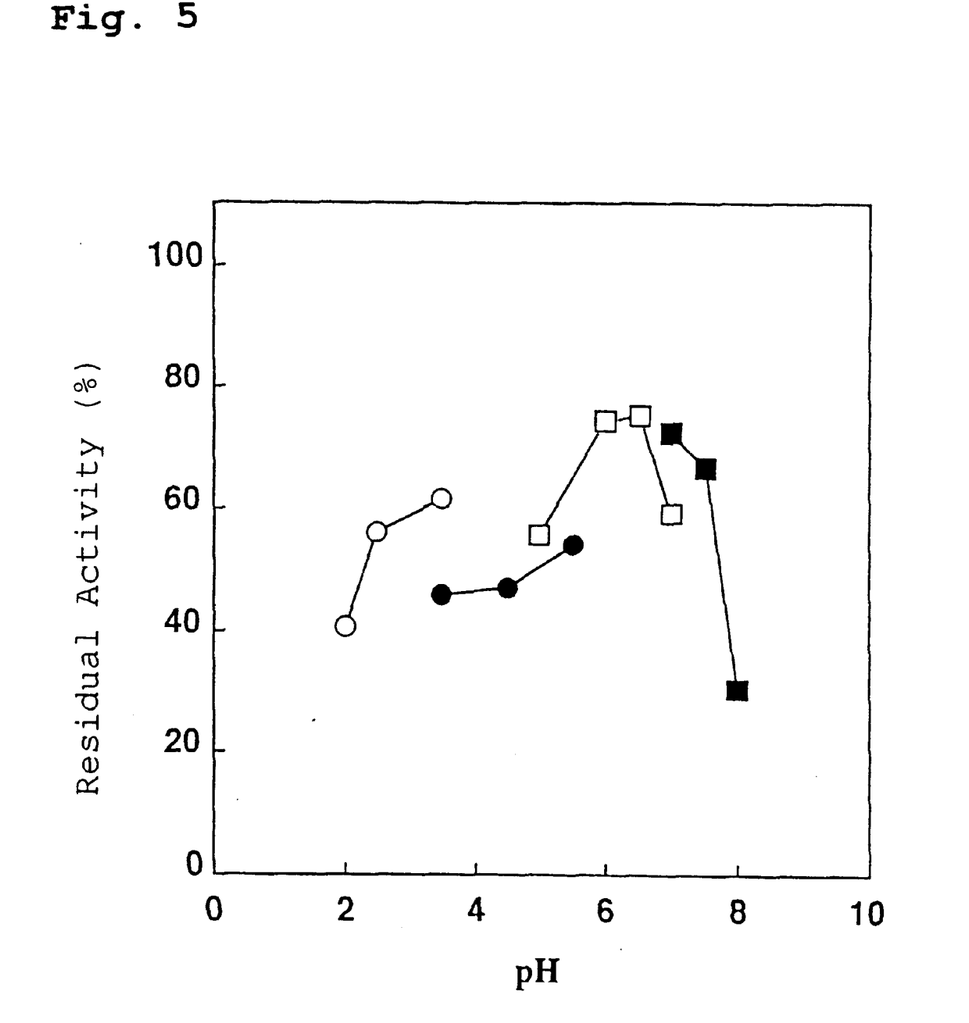
FIG. 5 shows the pH stability of phytase II.
Figure 6:
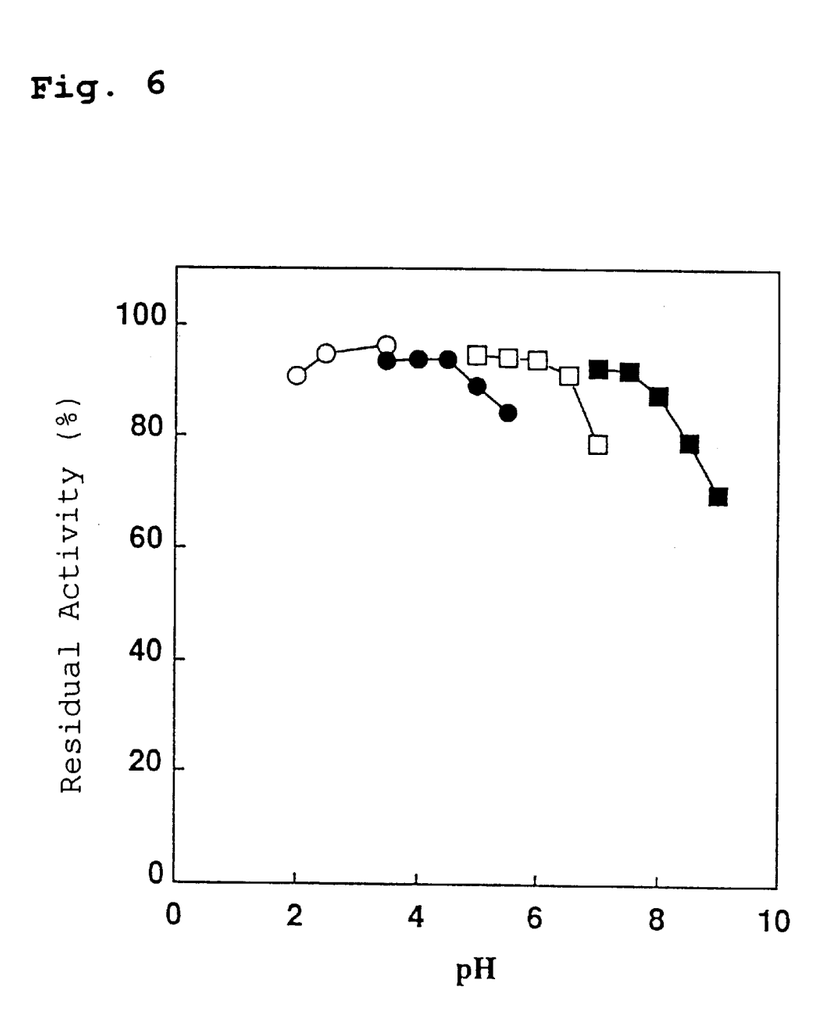
FIG. 6 shows the pH stability of phytase III.

② pH stability: After the enzyme solution was kept at 30° C. for 60 minutes in 50 mM buffer below, the activity was measured according to the standard activity measurement method.

| Glycine-HCl buffer | pH 2.0 to 4.0 |
| Acetic acid-sodium acetate buffer | pH 4.0 to 5.5 |

| | -continued | |
|---|---|---|
| MES buffer (Good buffer) | | pH 5.5 to 7.0 |
| Tris-HCl buffer | | pH 7.0 to 9.0 |

The results are shown in FIGS. 4, 5 and 6.

Phytase I was stable in the range of pH 5.5 to 6.5, phytase II in the range of pH 6.0 to 7.0, and phytase III in the range of pH 2.0 to 8.0.

Figure 7:
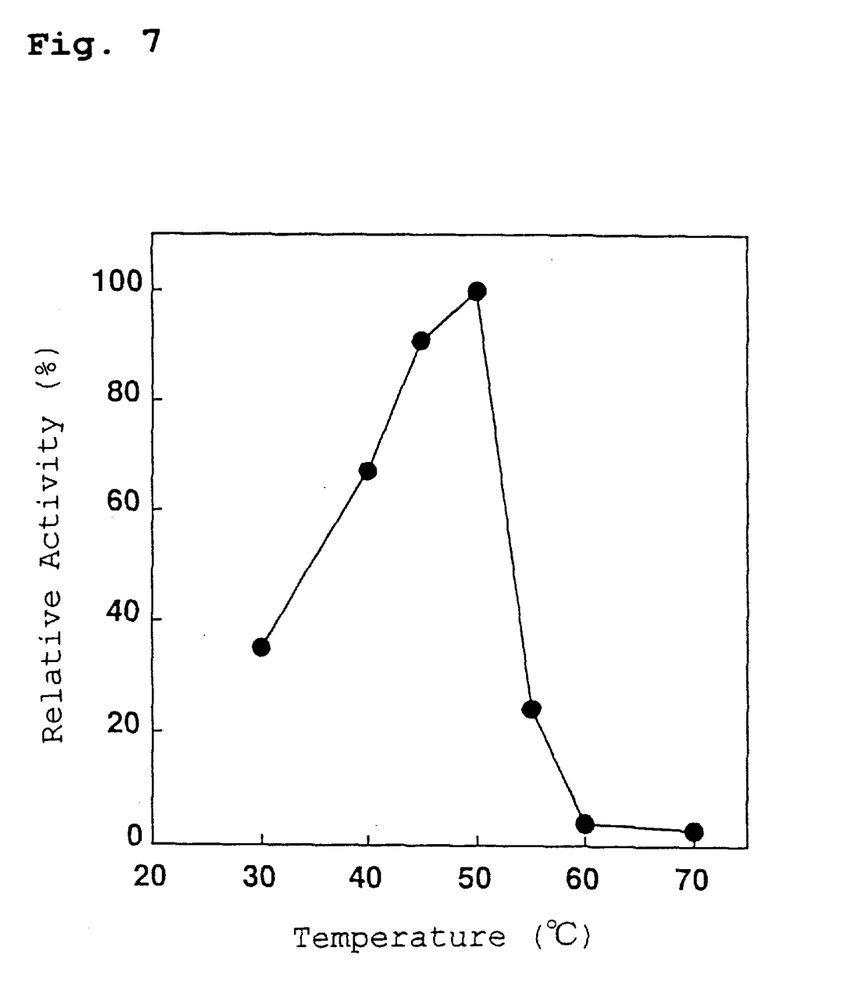
FIG. 7 shows the optimum temperature of phytase I.
Figure 8:
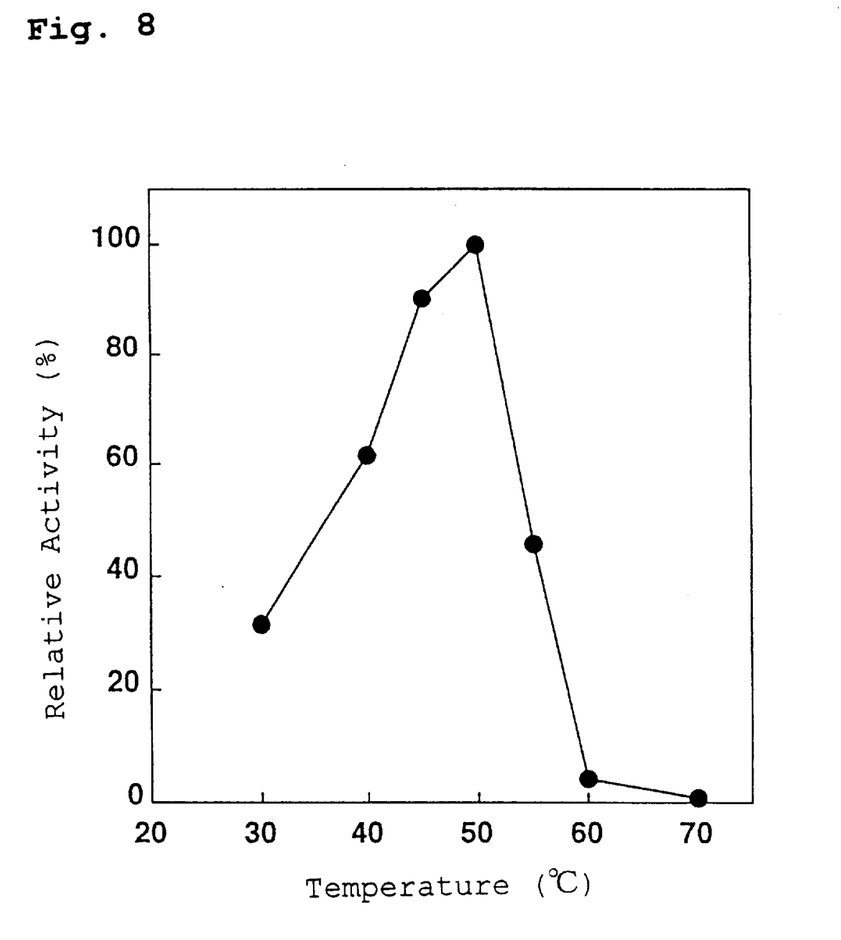
FIG. 8 shows the optimum temperature of phytase II.
Figure 9:
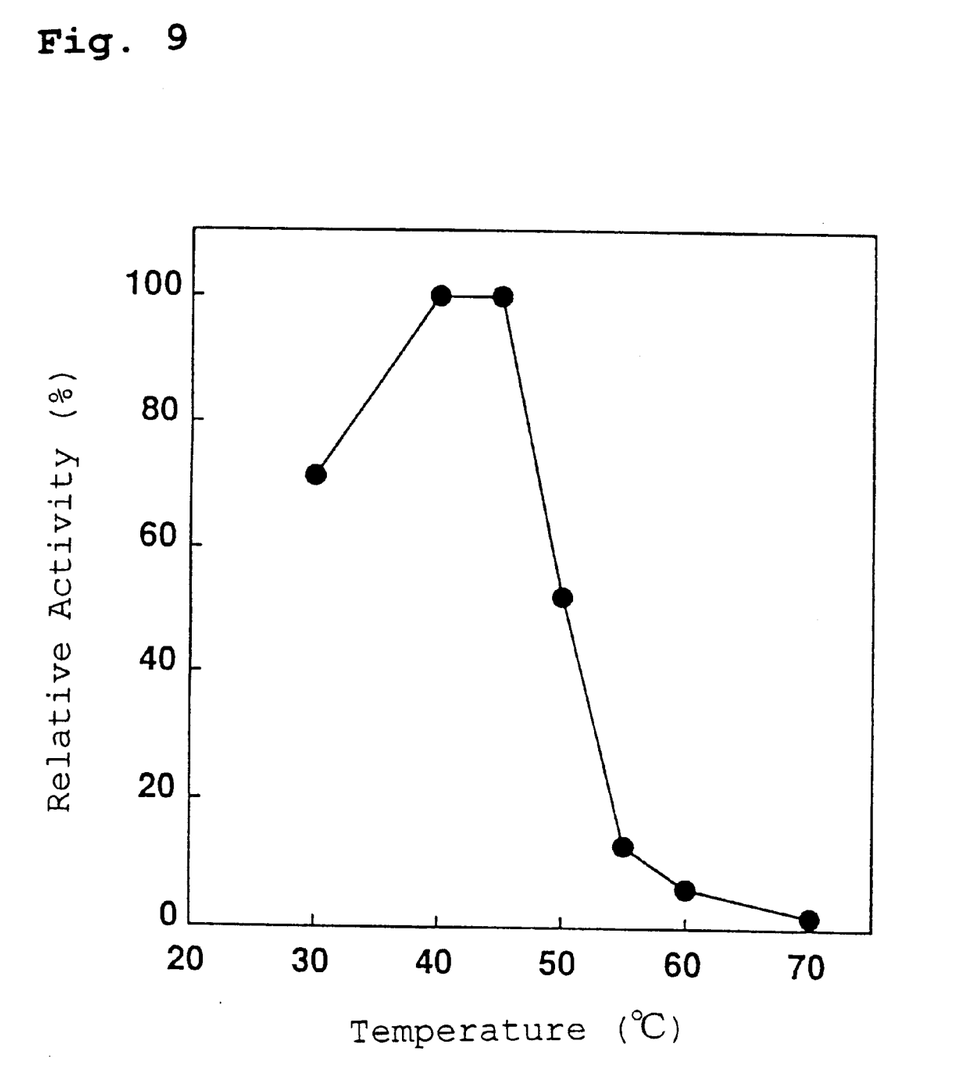
FIG. 9 shows the optimum temperature of phytase III.

③ Optimum temperature: After the reaction temperature used for measuring the enzyme activity was varied in the range of 30 to 70° C., the activity at each temperature was measured according to the standard activity measurement method.

The results are shown in FIGS. 7, 8 and 9.

Both phytases I and II showed the maximum activity at 50° C. Phytase III showed the maximum activity at 45° C.

Figure 10:
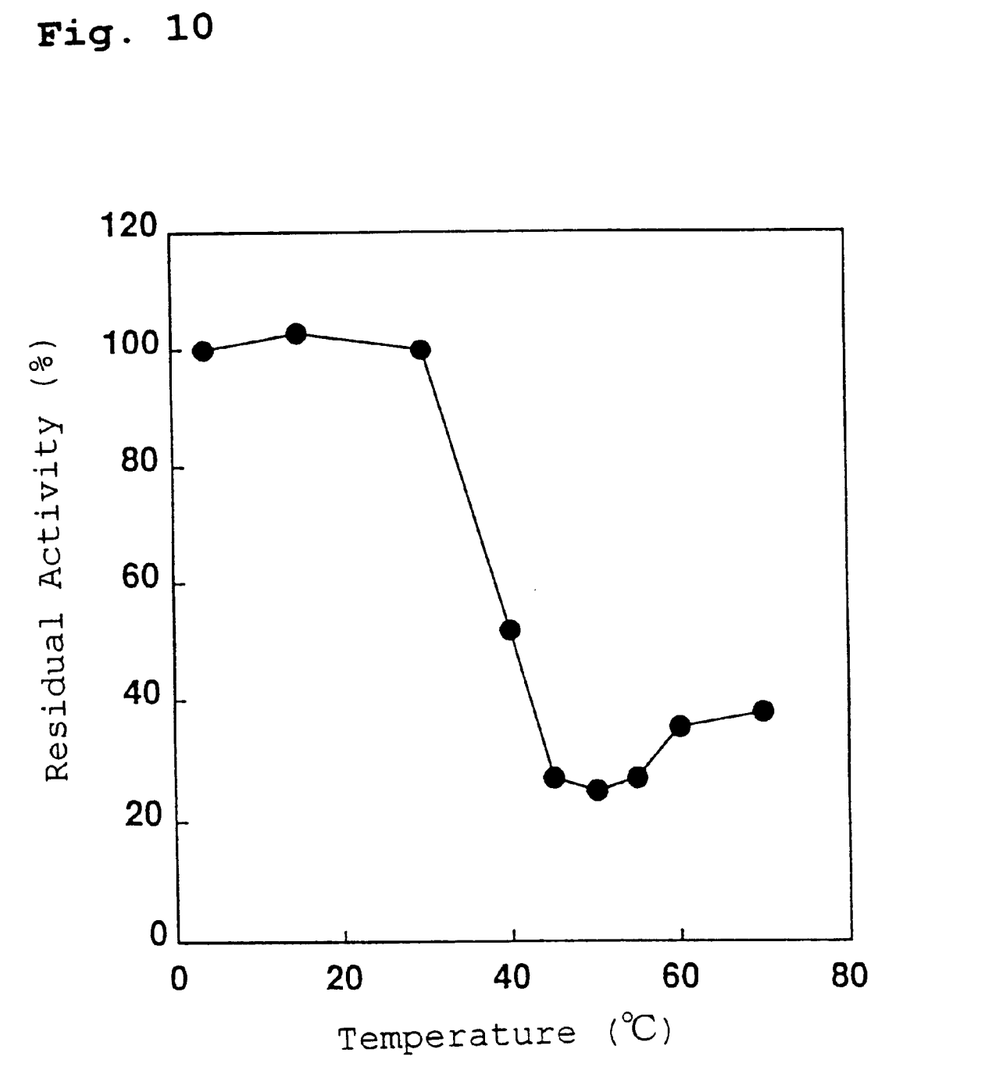
FIG. 10 shows the temperature stability of phytase I.
Figure 11:
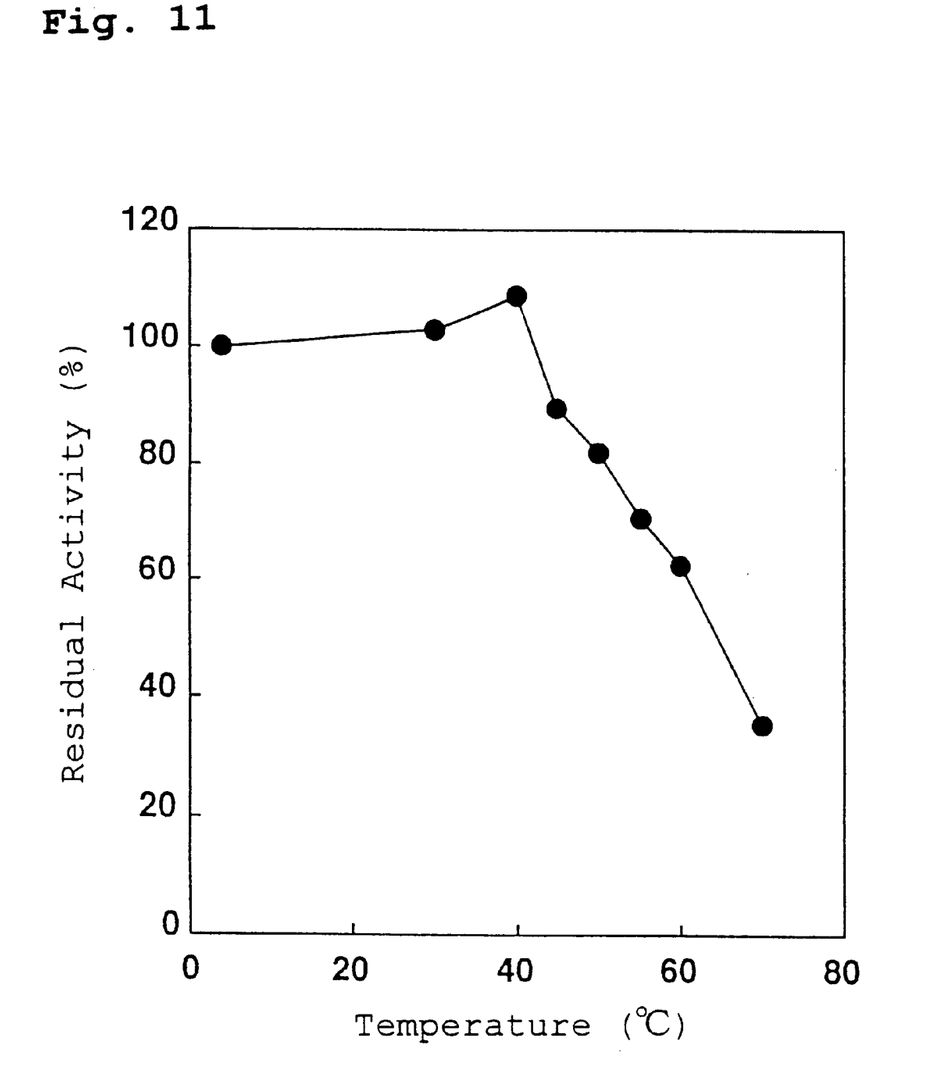
FIG. 11 shows the temperature stability of phytase II.
Figure 12:
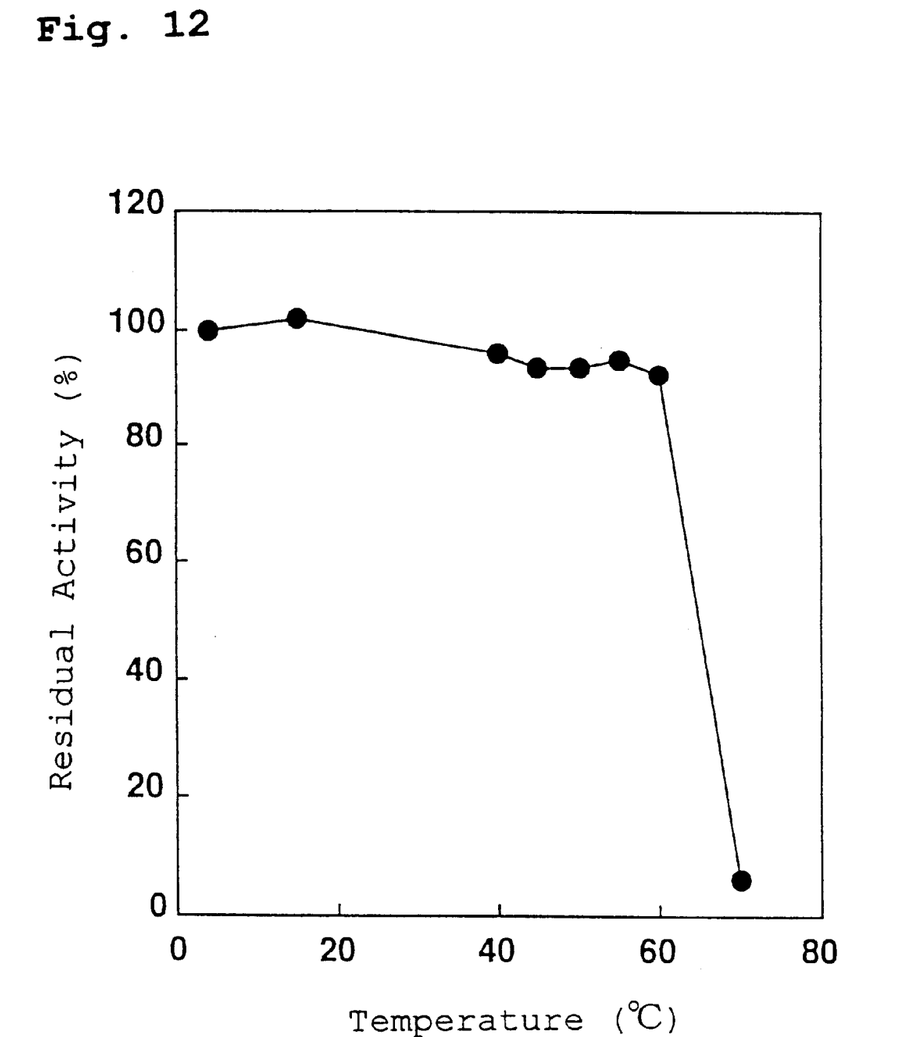
FIG. 12 shows the temperature stability of phytase III.

④ Temperature stability: After the enzyme solution was kept at 4 to 70° C. for 10 minutes in 20 mM MES buffer (pH 6.0), the activity was measured according to the standard activity measurement method.

The results are shown in FIGS. 10, 11 and 12.

Phytase I was stable up to 35° C., phytase II up to 50° C., and phytase III up to 60° C.

⑤ Substrate specificity: The activity was determined according to the standard activity measurement method using each substrate prepared at 2.5 mM, and the results are shown in Table 1.

Any of phytases I, II and III had low substrate specificity.

TABLE 1

Substrate Specificity of the Phytases

| | Phytases | | |
|---|---|---|---|
| | I | II | III |
| Phytic acid | 100 | 100 | 37.8 |
| p-Nitrophenylphosphate | 224 | 53.9 | 100 |
| D-myo-inositol (1,4)-diphosphate | 99.6 | 53.5 | 93.9 |
| D-myo-inositol 2-phosphate | 53.9 | 11.1 | 43.5 |
| D-myo-inositol 1-phosphate | 87.9 | 17.7 | 53.5 |
| Glucose 6-phosphate | 152 | 30.9 | 128 |
| Fructose 6-phosphate | 211 | 29.6 | 95.0 |
| Adenosine triphosphate | 223 | 42.0 | 191 |

⑥ Molecular weight: The molecular weight was determined by gel filtration on TOYO-pearl HW-55F (column size 1.0×119 cm, 93.4 ml). A calibration curve was prepared using RNase A (M. W. 15500), ovalbumin (M. W. 42700), albumin (M. W. 63300), and aldolase (M. W. 163000) as standards.

The molecular weights of phytases I, II and III were 80 to 100, 120 and 140 kDa, respectively.

⑦ Isoelectric point: Phytase was applied to a Polybuffer exchanger PBE94 column (Pharmacia) previously equilibrated with 20 mM MES buffer (pH 6.0), and then eluted with 10% Polybuffer 74-HCl (pH 4.0). The isoelectric point of the phytase was determined by measuring the pH value of the elution fraction with a pH meter.

The results indicated that the isoelectric points of phytases I, II and III were pI 5.7, 4.8 and 5.2, respectively.

Example 5

(Analysis of N-terminal Amino Acid Sequence of Phytase III)

To determine the molecular weight of phytase III by SDS-polyacrylamide gel electrophoresis (SDS-PAGE), the enzyme was highly purified. To 12.5% multi-gel (Daiichi Kagaku K. K.), 50 μl of the enzyme purified according to Example 2 was applied and subjected to native-PAGE according to the method of B. J. Davis [Ann. N. Y. Acad. Sci., 121 404–427 (1964)]. After electrophoresis, the gel was sliced into pieces of 5 mm in width and immersed in 1 ml of 20 mM MES buffer (pH 6.0) and stored at 4° C. for 12 hours so that the enzyme was extracted. After the extract was concentrated 15- to 20-fold in a rotary evaporator, a phytase fraction was identified by the standard activity measurement method described in the Reference Example. Under reduction with mercaptoethanol, 10 μl of the active fraction was subjected to SDS-PAGE to give high-purity phytase III. From this result, the molecular weight of phytase III by SDS-PAGE was determined to be about 65 kDa.

Analysis of the N-terminal amino acid sequence of phytase III was performed in the following manner. That is, phytase III purified in Example 2 was subjected to SDS-PAGE under reduction with 2-mercaptoethanol and then transferred electrically to a PVDF membrane (ProBlott, Perkin Elmer) according to the method of P. Matsudaira [J. B. C., 262, 10035–10038 (1987)]. The membrane having the enzyme transferred thereto was stained with Coomassie Blue, and its band with a molecular weight of about 65 kDa was cut out and analyzed for its N-terminal amino acid sequence by a method recommended by manufacturer's instructions in a gas-phase protein sequencer (PPSQ-10, Shimadzu Corporation). The amino acid sequence thus obtained is shown in SEQ ID NO:1. As a result of homology examination of the amino acid sequence described herein by using a protein data base, it was found to be a novel sequence.

INDUSTRIAL APPLICABILITY

According to the present invention, there can be provided phytases having low Km values for phytic acid and a process for producing the phytases by use of a microorganism having the ability to produce and accumulate the phytases.

The phytases can be added to feed to decompose phytic acid as anti-trophic factor contained in feed thereby improving the nutritive values of feed and simultaneously enabling efficient utilization of phosphate released by said decomposition.

What is claimed is:

1. An isolated phytase derived from a microorganism belonging to the genus Monascus and having a Michaelis constant of 10 to 110 μM when phytic acid is used as a substrate.

2. An isolated phytase according to claim 1, wherein the phytase has the following physicochemical properties:
1) Km: 27 μM when phytic acid is used as a substrate;
2) optimum pH: pH 5.5;
3) pH stability: stable in the range of pH 5.5 to 6.5;
4) optimum temperature: 50° C.;
5) temperature stability: stable up to 35° C.;
6) substrate specificity: acting on phytic acid, p-nitrophenylphosphate, D-glucose-6-phosphate, fructose-6-phosphate, D-myo-inositol-2-phosphate, D-myo-inositol-1-phosphate, D-myo-inositol-1,4-diphosphate, and adenosine triphosphate as the substrate;
7) molecular weight: about 80 to 100 kDa (gel filtration method); and
8) isoelectric point: pI 5.7 (chromatofocusing method).

3. A phytases according to claim 1, wherein the microorganism belonging to the genus Monascus is *Monascus anka* IFO30873.

4. A process for producing phytases which comprises (A) culturing a microorganism belonging to the genus Monascus and having the ability to form and accumulate a phytase having a Michaelis constant of 10 to 110 μM for phytic acid as a substrate until the phytase is formed and accumulated, and (B) recovering the phytase from the culture.

5. The process according to claim 4, wherein the phytase is a phytase having the following physicochemical properties:
1) Km: 27 μM when phytic acid is used as a substrate;
2) optimum pH: pH 5.5;
3) pH stability: stable in the range of pH 5.5 to 6.5;
4) optimum temperature: 50° C.;
5) temperature stability: stable up to 35° C.;
6) substrate specificity: acting on phytic acid, p-nitrophenylphosphate, D-glucose-6-phosphate, fructose-6-phosphate, D-myo-inositol-2-phosphate, D-myo-inositol-1-phosphate, D-myo-inositol-1,4-diphosphate, and adenosine triphosphate as the substrate;
7) molecular weight: about 80 to 100 kDa (gel filtration method); and
8) isoelectric point: pI 5.7 (chromatofocusing method).

6. The process according to claim 4, wherein the microorganism belonging to the genus Monascus is *Monascus anka* IFO30873.

7. An animal feed comprising a phytase obtained from a microorganism belonging to the genus Monascus and having a Michaelis constant of 10 to 110 μM when using phytic acid as a substrate.

* * * * *